United States Patent
Haras

(10) Patent No.: US 7,657,074 B2
(45) Date of Patent: Feb. 2, 2010

(54) METHOD FOR DETERMINING ACQUISITION PARAMETERS FOR A MEDICAL TOMOGRAPHY DEVICE, AND AN ASSOCIATED APPARATUS

(75) Inventor: Gabriel Haras, Muecke (DE)

(73) Assignee: Siemens Aktiengesellschaft, Munich (DE)

( * ) Notice: Subject to any disclaimer, the term of this patent is extended or adjusted under 35 U.S.C. 154(b) by 231 days.

(21) Appl. No.: 11/330,238

(22) Filed: Jan. 12, 2006

(65) Prior Publication Data
US 2006/0153436 A1 Jul. 13, 2006

(30) Foreign Application Priority Data
Jan. 13, 2005 (DE) .................. 10 2005 001 681

(51) Int. Cl.
*G06K 9/00* (2006.01)
(52) U.S. Cl. .................. 382/131; 378/4; 378/21
(58) Field of Classification Search .................. 382/131; 378/4, 21
See application file for complete search history.

(56) References Cited

U.S. PATENT DOCUMENTS

| | | | |
|---|---|---|---|
| 6,829,323 B2 * | 12/2004 | Toth et al. ...................... | 378/4 |
| 6,898,302 B1 * | 5/2005 | Brummer ..................... | 382/131 |
| 6,944,269 B2 | 9/2005 | Schmitt | |
| 7,031,423 B2 * | 4/2006 | Tsukagoshi ..................... | 378/4 |
| 7,039,163 B2 * | 5/2006 | Popescu et al. ............. | 378/109 |
| 2003/0108154 A1 * | 6/2003 | Schmitt ....................... | 378/115 |

FOREIGN PATENT DOCUMENTS

DE 101 60 611 A1 6/2003

OTHER PUBLICATIONS

Kachelriess et al., "Strategies for Dose Reduction and Improved Image Quality in MSCT", 2004, Springer, XVI, 35-45.*

* cited by examiner

*Primary Examiner*—Brian P Werner
*Assistant Examiner*—Katrina Fujita
(74) *Attorney, Agent, or Firm*—Harness, Dickey & Pierce, P.L.C.

(57) ABSTRACT

A method and apparatus are disclosed for determining, with particular simplicity, an acquisition parameter for a medical tomography device. It is provided here to make an original image available for a selection, selection of the original image being used to select an original parameter set assigned thereto as acquisition parameter set. In order to compile the original image, it is provided here to modify a basic tomographic raw data record before carrying out a 3D reconstruction by means of a noise algorithm for simulating a virtual image quality measure.

19 Claims, 3 Drawing Sheets

METHOD FOR DETERMINING ACQUISITION PARAMETERS FOR A MEDICAL TOMOGRAPHY DEVICE, AND AN ASSOCIATED APPARATUS

The present application hereby claims priority under 35 U.S.C. §119 on German patent application number DE 10 2005 001 681.2 filed Jan. 13, 2005, the entire contents of which is hereby incorporated herein by reference.

FIELD

The invention generally relates to a method for determining an acquisition parameter set. The parameter set may include, for example, a number of prescribed acquisition parameters. The method may further be for a medical tomography device, for example. The method may include making an original image available for selection, with selection of the original image being used to select an original parameter set assigned thereto as acquisition parameter set. The invention also generally relates to an apparatus for carrying out the method.

BACKGROUND

Tomography generally denotes an imaging medical slice recording method that enables the production of three-dimensional image information relating to a body region of a patient that is to be examined. In this sense, the term tomography includes computed tomography, in particular, but also magnetic resonance (MR) tomography.

Computed tomography on the one hand, and MR tomography on the other hand, resemble one another—irrespective of the different measurement principle—to the effect that firstly a raw data record of the body region of the patient that is to be examined is firstly recorded, and the desired three-dimensional image information is calculated therefrom only later by applying mathematical algorithms. This calculation step is denoted below as 3D reconstruction.

Computed tomography and MR tomography are also similar to one another in that the image quality of the image (or tomogram) calculated by way of 3D reconstruction is a function of a multiplicity of acquisition parameters of the respective tomography device. In the case of computed tomography, the acquisition parameters particularly include technical parameters such as the tube voltage and the tube current of the X-ray tube, the table feed speed, the tube rotation time, the collimation, etc. In the wider sense, the acquisition parameters are taken below also to include variables that characterize the image processing, in particular the image reconstruction. Thus, the acquisition parameters of the latter type chiefly include the parameters of the 3D reconstruction algorithm, in particular the slice thickness and the increment.

Because of the multiplicity of the acquisition parameters and the sometimes complex interaction between various acquisition parameters, the user of a tomography device requires considerable experience in order to find a favorable configuration of the acquisition parameters straight away with regard to a specific examination to be undertaken and to a specific patient. On the one hand, an unfavorable parameter configuration can result in a low, sometimes even inadequate image quality that, in the extreme case, can even necessitate repeating the examination. On the other hand, parameters can be selected that are associated with a comparatively high dose but, with reference to the targeted examination, are associated as a rule with no, or only a slight gain in information by comparison with a standard image quality. Both cases result in an unnecessary, since additional burden, in particular radiation burden, for the patient, an additional loading of the medical device and an unnecessary loss of time.

Modern tomography devices frequently offer a multiplicity of different protocols with stipulations for the setting of the acquisition parameters, in order to alleviate the complex parameter setting for the user. However, these protocols generally have to be adapted manually to the specific problem and/or the patient profile (body size, weight, . . . ). Again, in modern computer tomographs the tube current is matched to the patient profile in a semi-automated fashion.

Particularly for the examination of children, the provision of such protocols has, however, so far led at best to a comparatively slight alleviation, even more so as precisely with children the setting of the acquisition parameters that is "optimal" for a specific problem can vary substantially as a function of growth and development. On the other hand, there is frequently a certain deficit of experience precisely in the case of the tomographic examination of children. On the one hand, the operating staff of a tomography device, in particular a radiologist entrusted with a computer tomograph, frequently has only a comparatively slight specialized knowledge of the particular requirements for the tomographic examination of children. On the other hand, in turn, specialized child radiologists frequently have no continuous access to a tomography device, and can therefore obtain only limited experience of the particular unit.

It is proposed in DE 101 60 611 A1, for the purpose of a simplified setting of acquisition parameters of an imaging medical examination unit, to undertake the acquisition parameters in the generic sense indirectly by selecting a stored exemplary image originating from an earlier examination. Here, the exemplary image is modified by changing the contrast and the brightness in order to simulate various parameter settings of equipment parameters. When an image modified in such a way is selected, the simulated parameter settings are taken over as actual equipment settings.

The known method is provided in general for use with imaging medical methods, but in particular is set up and suitable for two-dimensional X-ray photographic methods. In these X-ray photographic methods, an unfavorable parameter selection leads to an "underexposure" or "overexposure" that can be simulated by varying contrast and brightness of the exemplary image. By contrast, the known method is little suited to simulating the parameter settings in the case of a tomography device.

SUMMARY

It is an object of at least one embodiment of the invention to configure such a method favorably for determining suitable acquisition parameters for use in conjunction with a tomography unit. At least one embodiment of the invention may also include on an object of specifying an apparatus that is particularly suitable for carrying out the known method.

It is provided thereby to undertake the selection of an acquisition parameter set for a medical tomography device with the aid of an original image for whose compilation a basic tomography raw data record (raw data record below) is already modified before carrying out a 3D reconstruction by the application of a noise algorithm so as to simulate a virtual image quality measure deviating from the image quality of the original raw data record.

It has emerged that, starting from one and the same original raw data record, and thus from the same patient, original images can be realistically simulated in various image quality stages by adding noise to the raw data. In particular, low dose artifacts in the original images that are characteristic on the raw data level are simulated with particular realism by the addition of noise. The effect of a change in one or more acquisition parameters can thereby be displayed to the user in a particularly flexible and realistic fashion.

In addition, the modification carried out on the raw data level opens up the possibility of reconstructing in a different way the same picture modified with regard to image quality. In particular, the user thereby has the possibility of testing the interaction between the technical acquisition parameters (for example tube current, tube voltage, etc.) with the parameters of the 3D reconstruction. For example, in this way the user can find configurations of the acquisition parameters in the case of which a setting of the technical acquisition parameters that is rather "poor" per se with regard to image quality can be compensated by suitable parameterization of the 3D reconstruction such that the user in this way attains a particularly low burden on the patient without appreciable loss of information with regard to the targeted examination.

An (X-ray) dose value may be used, for example, as image quality measure, particularly when the method is applied to computed tomography. The image quality measure in this way simultaneously represents a measure of the patient burden associated with the imaging.

In an advantageous embodiment of the method, the actual selection of an original image by the user is preceded by a preselection in the course of which an original image or a number of original images is/are preselected in accordance with at least one patient parameter and is/are made available to the user for selection. Use is made here as patient parameter of a patient-specific datum such as the weight, the body size, the age and/or the sex of the patient to be examined. A datum referring to a body region to be examined (for example thorax, head, etc.) is also denoted in a wider sense as a patient parameter.

It may be provided, for example, that a raw data record is compiled in each case from a group of a number of original images that all—according to their membership of the same raw data record—reflect the same examination situation and are assigned to the same patient but which differ from one another with regard to the virtual image quality measure. The original images of a group therefore show the same image in different qualitative stages. By comparing the various original images of a group, a user can therefore directly compare various configurations of the acquisition parameters.

It may be provided, for example, that in the case of the selection process to be undertaken by the user, such a group of original images is always preselected as a whole according to the specified patient parameter(s), and made available to the user for the selection. The individual original images of the preselected group are expediently shown to the user alternatively for the selection and so the user can "leaf through" these original images to search for a particularly suitable image quality. It is expediently provided that the original images can be sorted here in various ways according to the user's wishes, for example by X-ray dose, by image quality, etc.

In order to alleviate this selection process, it is expediently provided that in addition to an original image displayed for the selection there is displayed simultaneously a standard original image of the same group that corresponds to a previously determined standard image quality.

It is expediently provided for a further simplification of the selection process that, at the same time as each original image is made available for the selection is being displayed, so is the image quality measure assigned to this original image, and thus, in particular, the dose value used as image quality measure. This permits the user either to better assess the original image displayed with regard to its image quality and to deduce the patient burden associated with the corresponding original parameter set.

It is advantageously visualized in addition whether the dose value assigned to the original image displayed is comparatively high or low for the selected patient profile and the selected body region, or is located in a middle range. When the method is used for a computer tomograph with automatic adaptation of the tube current to the patient profile, an abstract reference controlled variable of the image quality that is required for the adaptation is displayed as an alternative, or in addition to the absolute (X-ray) dose.

With reference to the apparatus provided for carrying out at least one embodiment of the above-described method, the apparatus includes a selection system having an original memory in which at least one original image compiled according to at least one embodiment of the above-described method. However, a multiplicity of such original images may be stored, for example. The selection system further includes a selection module that is designed to make one or more of the stored original images available for the selection and, given the selection of an original image, to output an original parameter set assigned thereto as acquisition parameter set.

The selection system also may include, for example, a preselection module that is designed to preselect one or more original images from the original memory with the aid of at least one patient parameter.

In order to compile the original images, the apparatus further expediently comprises an original compilation system. In an example embodiment, this includes a simulation module, that is designed to modify a raw data record of the tomography device by applying a noise algorithm in order to simulate a virtual image quality measure with regard to the original image. The original compilation system further includes a 3D reconstruction module that is designed to derive a tomogram as original image from the modified raw data record. The 3D reconstruction module is here downstream of the simulation module, and so the modification of the original images is performed on the raw data level. Finally, the original compilation system includes an original memory for storing the or each original image.

The selection system and the original compilation system may be, for example, embodied as hardware and software components of a data processing system. This data processing system can be directly connected to the associated tomography device such that given selection of an original image, the associated original parameter set is taken over directly as acquisition parameter set onto the tomography device, or new raw data records can be transmitted from the tomography device to the original compilation system.

However the apparatus may be designed, for example, as a stand-alone unit that can be operated separately and independently of the tomography device. This advantageously enables the user also to undertake to optimize acquisition parameters with regard to a planned examination precisely whenever the tomography device is not available or not available continuously for test purposes. In this case, the selected acquisition parameter set is firstly output in the form of an electronic file or of a paper printout and, if appropriate, transmitted to the tomography device at a later point in time.

The selection system is optionally integrated together with the original compilation system in a common software package and implemented on a single data processing system. The original memory of the selection system and the original memory of the original compilation system are, in particular, identical in this case. Alternatively, the selection system and the original compilation system can, for example also be designed as independent software applications and therefore, in particular, also be implemented on different data processing systems. For example, it can be provided that only the selection system is present at the user end, while the original compilation system is available for compiling the original images at the manufacturer end. The original memory of the original compilation system, and the original memory of the selection system can be designed here as physically different memory units, only the memory contents being transmitted using current data transmission device(s)/method(s), from the original compilation system to the selection system after compilation of the original images.

BRIEF DESCRIPTION OF THE DRAWINGS

An example embodiment of the invention is explained in more detail below with the aid of the drawing figures, in which.

Mutually corresponding parts and variables are always provided with the same reference symbols in all the figures.

DETAILED DESCRIPTION OF THE EXAMPLE EMBODIMENTS

Figure 1:
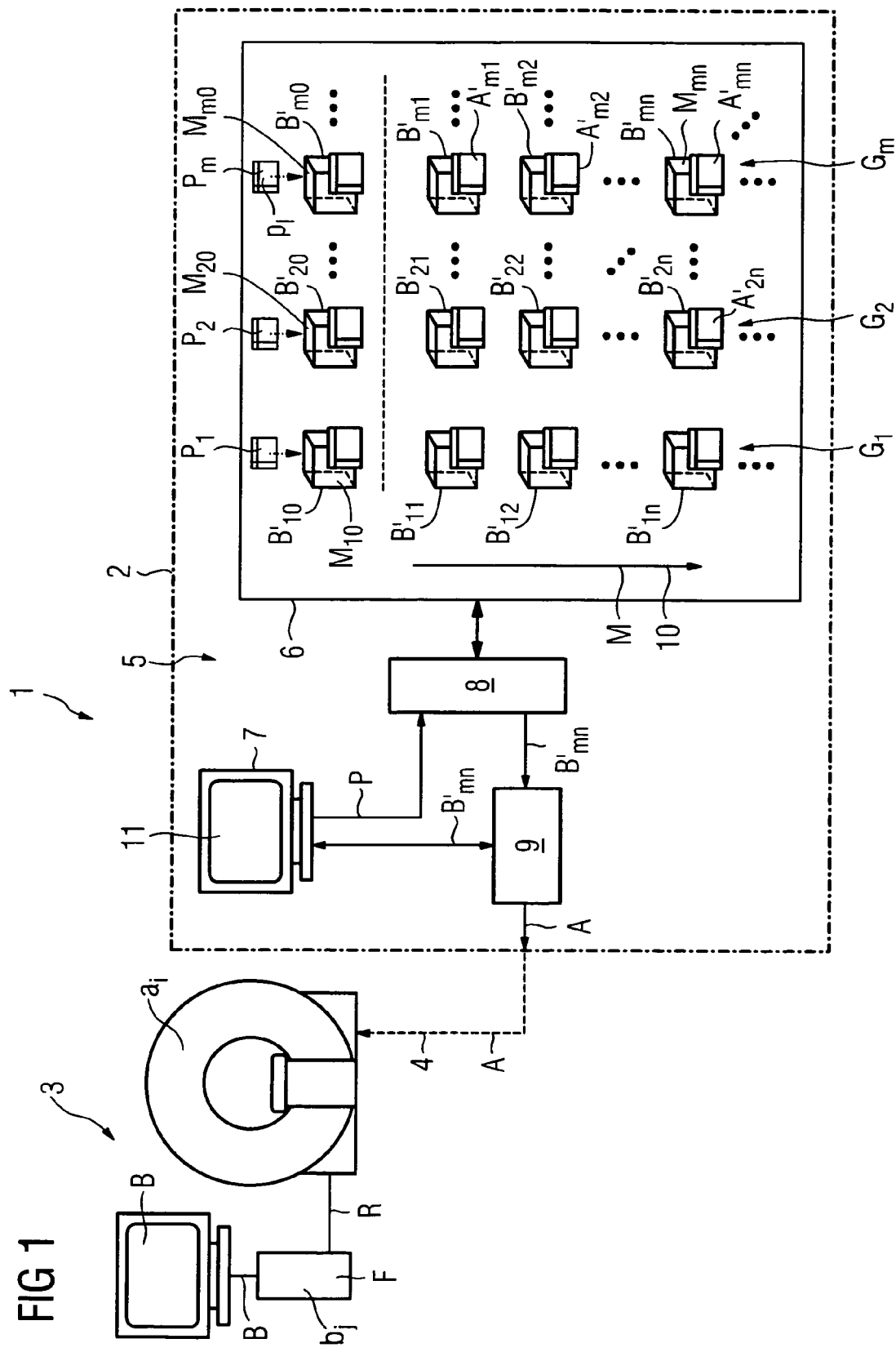
FIG. 1 shows a schematic block diagram of a selection system of an apparatus for determining acquisition parameters for a medical tomography device.

A selection system 2 for determining an acquisition parameter set A for a medical tomography device 3 is illustrated schematically in FIG. 1 as a component of an apparatus 1. The tomography device 3 is a computer tomograph. The apparatus 1 is assigned to the tomography device 3 if the acquisition parameter set A produced by the apparatus 1 includes values for those acquisition parameters $a_i$ and $b_j$ (i,j=1, 2, 3, . . . ) that must be specified in order to record an image B by using the tomography device 3.

On the one hand, the acquisition parameters $a_i$, $b_j$ include technical acquisition parameters $a_i$ that parameterize the electrical and mechanical functions of the tomography device 3. The technical acquisition parameters $a_i$ include, in particular, the tube current and the tube voltage of an X-ray tube of the tomograph, the table feed speed, tube rotation time, collimation etc. Further acquisition parameters $b_j$ parameterize a 3D reconstruction algorithm F by means of which the three-dimensional image B (or tomogram) of a recorded body volume of a patient is calculated from a raw data record R firstly produced by the tomography device 3. The acquisition parameters $b_j$ comprise, in particular, slice thickness and increment.

The apparatus 1 is preferably not connected directly and continuously to the tomography device 3. Rather, the apparatus 1 can be used independently of the tomography device 3, and can be connected to the tomography device 3 only as required via a data transmission connection 4, in particular a computer network.

The selection system 2 is designed as part of a data processing system 5 and includes an original memory 6 that is a component of a memory module of the data processing system 5, and input/output device(s) 7 such as display screen, keyboard, mouse, etc. The selection system 2 further includes a preselection module 8 and a selection module 9. Both modules 8 and 9 are preferably designed as software components of the data processing system 5.

Figure 3:
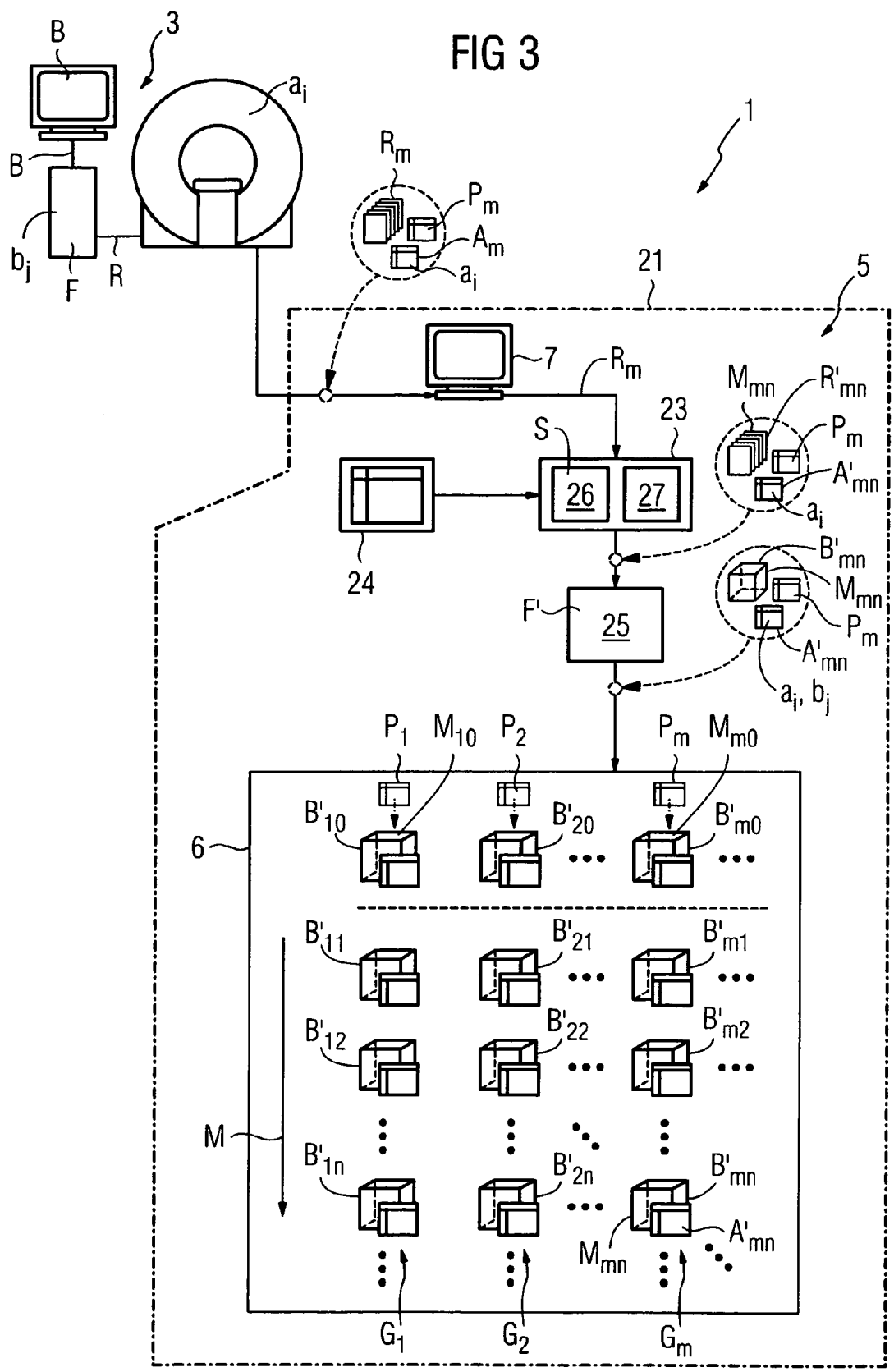
FIG. 3 shows an illustration according to FIG. 1 of an original compilation system of the apparatus in accordance with FIG. 1.

A multiplicity of original images $B'_{mn}$ (m,n=1, 2, 3, . . . ) are stored in the original memory 6. Each original image $B'_{mn}$ has the form and the data format of an image B as produced in the course of a recording process of the tomography device 3. Each original image $B'_{mn}$ also originates from a raw data record $R_m$ (m=1, 2, 3, . . . ; s. FIG. 3) recorded at an earlier point in time by way of the tomography device 3, and is produced therefrom in a way described below in more detail.

The original images $B'_{mn}$ stored in the original memory 6 are classified into a number of groups $G_m$ (m=1, 2, 3, . . . ). In the illustration in accordance with FIG. 1, each group $G_m$ is represented by a vertical row of original images $B'_{mn}$ whose counting index m agrees with the corresponding counting index m of the group $G_m$. The original images $B'_{21}$, $B'_{22}$, . . . , $B'_{2n}$, . . . thus belong to the group $G_2$, etc.

The original images $B'_{mn}$ of a group $G_m$ each come here from a common raw data record $R_m$. They therefore all originate from the same examination situation, and thereby also all image the same patient, in particular. Each group $G_m$ is correspondingly assigned a common patient parameter record $P_m$ (m=1, 2, 3, . . . ). Each patient parameter record $P_m$ includes values for prescribed patient parameters $p_l$ (l=1, 2, 3, . . . ). The patient parameters $p_l$ include a weight datum and a body size datum of the patient imaged by the raw data record $R_m$, and the specification of a recorded body region (for example, thorax).

The original images $B'_{mn}$ of the same group $G_m$ differ, by contrast, in an original parameter set $A'_{mn}$ that is assigned to each original image $B'_{mn}$ and has the structure of the acquisition parameter set A and to this extent specifies values for the acquisition parameters $a_i$, $b_j$. Each original image $B'_{mn}$ is further assigned an image quality measure $M_{mn}$. Here, a dose value assigned to the respective original image $B'_{mn}$ is used as image quality measure $M_{mn}$. The original images $B'_{mn}$ of a group $G_m$ are selected in such a way that they differ from one another with regard to the respectively assigned image quality measure $M_{mn}$, and so the original images $B'_{mn}$ of a group $G_m$ are present in different stages of image quality. This is indicated schematically in FIG. 1 by a scale axis 10, schematically depicted in the region of the original memory 6, of the image quality measure M.

In relation to each group $G_m$, the original memory 6 further includes a standard original image $B'_{m0}$ (m=1, 2, 3, . . . ), that corresponds to a prescribed standard image quality measure $M_{m0}$ (m=1, 2, 3, . . . ).

The patient parameter record $P_m$, the original parameter set $A'_{mn}$ and the image quality measure $M_{mn}$ are assigned to each original image $B'_{mn}$, $B'_{m0}$ as so-called metadata that are included, in particular in a header of the respective image file that is organized according to the DICOM standard.

In the course of the selection method, a user specifies via the input/output device(s) 7 a patient parameter set P that corresponds with regard to its data structure to the patient parameter set $P_m$ assigned to each original image $B'_{mn}$, and therefore specifies the values for the patient parameters $p_l$. For example, thus, the user specifies the weight and the body size of a patient, and a body region of the patient (for example thorax) via a user interface 11, indicated on the input/output device(s) 7, of the selection system 1. The patient parameter set P specified in such a way is fed to the preselection module 8. The latter determines that group $G_m$ whose assigned patient parameter set $P_m$ comes closest to the patient parameter set P with regard to the respective patient parameters $p_l$, and feeds the original images $B'_{mn}$ of the group $G_m$, preselected in such a way, and the associated standard original image $B'_{m0}$, to the selection module 9.

The selection module 9 makes the preselected original images $B'_{mn}$ available to the user for the selection by displaying the original images $B'_{mn}$ via the user interface 11.

Figure 2:
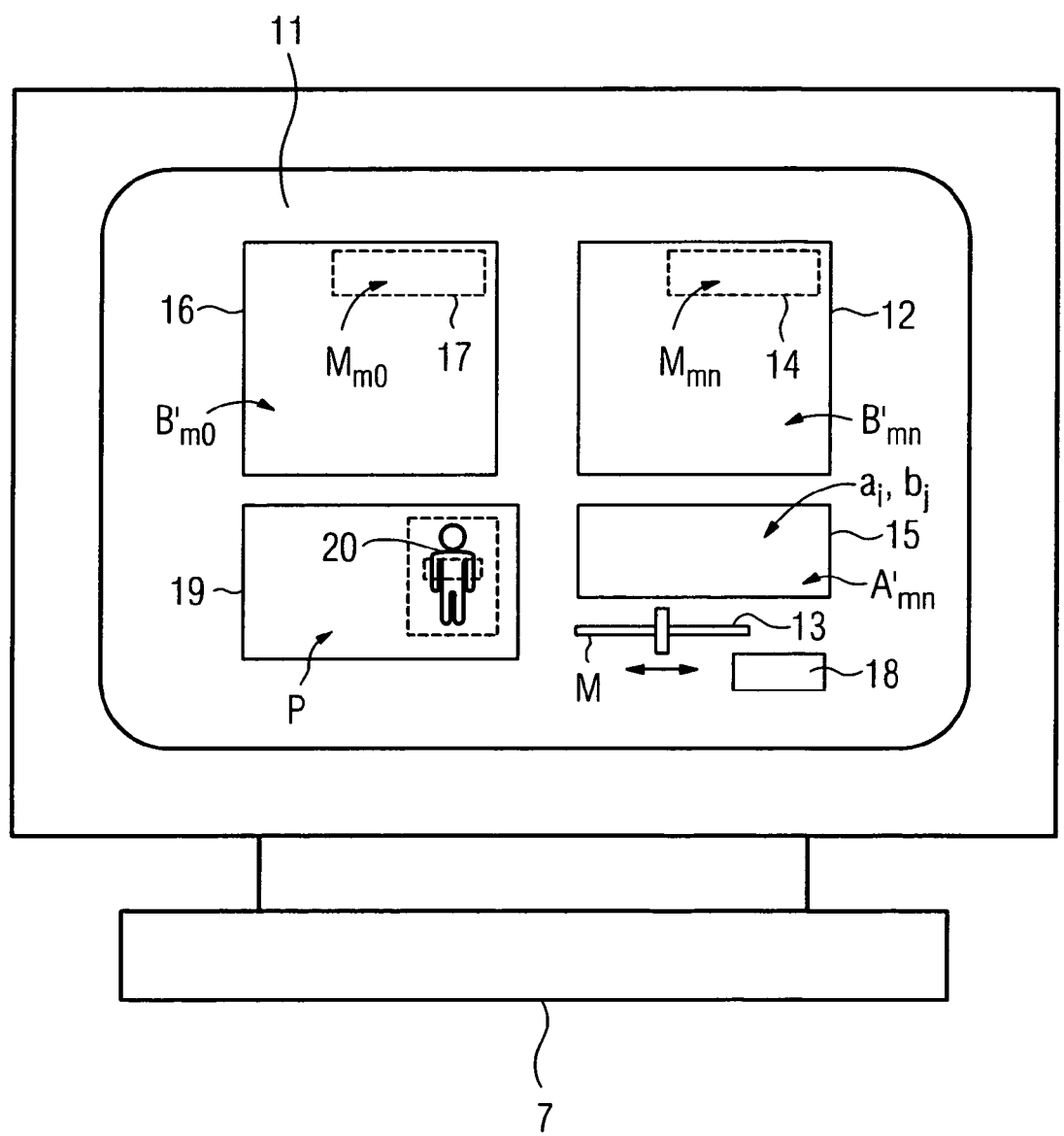
FIG. 2 shows a schematically simplified illustration of a user interface of the selection system in accordance with FIG. 1.

This is illustrated in more detail in FIG. 2 in a schematically simplified illustration of the user interface 11. The user interface 11 accordingly includes a display panel 12 in which in each case one of the preselected original images $B'_{mn}$ is displayed. By way of a control element 13 resembling a linear regulator, the user can set a desired image quality measure M and thereby determine which of the preselected original images $B'_{mn}$ is to be displayed. Here, it is always that original image $B'_{mn}$ whose assigned image quality measure $M_{mn}$ comes closest to the image quality measure M set via the control element 13 that is displayed. At the same time as the display of the original image $B'_{mn}$, the image quality measure $M_{mn}$ corresponding to the displayed original image $B'_{mn}$, that is to say the corresponding X-ray dose is displayed in a further display panel 14. The original parameter set $A'_{mn}$ assigned to the displayed original image $B'_{mn}$ is simultaneously displayed in a further display panel 15. The parameters $a_i$, $b_j$, displayed in the display panel 15, of the original parameter set $A'_{mn}$ can be varied by the user.

The user interface 11 comprises a further display panel 16, which corresponds to the display panel 12 and in which the standard original image $B'_{m0}$ associated with the preselected group $G_m$ is displayed. The display panel 16 is assigned a display panel 17 that corresponds to the display panel 14 and in which the associated standard image quality measure $M_{m0}$ is displayed.

The juxtaposition of an arbitrary original image $B'_{mn}$ with the standard original image $B'_{m0}$ enables the user to make a particularly good and simple estimate as to whether a customary image quality suffices to answer the question on which a planned examination is based. The possibility of directly comparing the displayed original image $B'_{mn}$ with the standard original image $B'_{m0}$ renders particularly obvious how much dosage can be spared, and with what loss or gain in image quality it is necessary to reckon here. The regulator setting of the control element 13 simultaneously visualizes for the user whether the currently set image quality is comparatively high or low with reference to the body region and the patient profile. The scale of the regulator 13 is correspondingly adapted.

If the user has found an original image $B'_{mn}$ that suffices with regard to the assigned image quality measure $M_{mn}$ for the planned examination, but on the other hand is associated with the smallest possible burden for the patient, the user actuates an actuation element 18 of the user interface 11 and thereby selects the displayed original image $B'_{mn}$. The selection module 9 thereupon outputs the original parameter set $A'_{mn}$ assigned to this preselected original image $B'_{mn}$ as acquisition parameter set A (see FIG. 1). The acquisition parameter A is optionally output by being directly transmitted to the tomography device 3 by storing the acquisition parameter set A in an electronic file, or by being output in paper form. A patient ID or name and date of birth are also stored as reference to a patient being examined.

Finally, the user interface 11 comprises an input panel 19 for inputting the patient parameters $p_1$. Inputting the patient parameters pi of the patient parameter set P is performed here optionally in text form and/or by way of graphic operating elements. For example, it is provided that the datum relating to the body region of the patient that is to be examined can be set graphically using a body scheme 20, in particular by mouse click.

In order to compile the original images $B'_{mn}$ the apparatus 1 further comprises an original compilation system 21 that is illustrated schematically in FIG. 3. The original compilation system 21 is implemented on the same data processing system 5 as the selection system 2. The selection system 2 and the original compilation system 21 are optionally integrated in a common software package or are designed as separate software applications that can be executed independently of one another. The original compilation system 21 in both cases likewise accesses the original memory 6 and the input/output device(s) 7. The original compilation system 21 further comprises a simulation module 23, a characteristic data base 24 and a 3D reconstruction module 25.

In order to compile a group $G_m$ of original images, $B'_{mn}$, the raw data record $R_m$ to be used as a base is firstly fed to the original compilation system 21. In the case of computed tomography, the raw data record $R_m$ is a series of two-dimensional x-ray projected images which image one volume region of a patient's body from different projection angles. Fed together with the raw data record $R_m$ are the corresponding patient parameter set $P_m$ (that includes in particular data relating to the body region examined, the patient's weight, the patient's size, the sex and/or the date of birth) and an associated parameter set $A_m$ that firstly specifies only the technical acquisition parameters $a_i$.

It is preferred to make use for the purpose of compiling the original images $B'_{mn}$ of raw data records $R_m$ of particularly high image quality, thus in particular raw data records $R_m$ whose assigned dose level assumes an upper limit with regard to the performance of the tomography device 3 or with regard to the medical acceptability of the applied dose.

The raw data record $R_m$ is fed to the simulation module 23 upon an appropriate instruction from a user.

The simulation module 23 comprises a noise module 26 in which a noise algorithm S is implemented. Noise is added to the raw data of the original raw data record $R_m$ by the noise algorithm S.

To add noise, the noise algorithm S adds noise to the raw data pixel by pixel, that is to say superimposes on the raw data a fluctuation pattern that randomly varies the data values of the raw data record $R_m$ irregularly, in particular within prescribed limits. The "strength" of the noise is prescribed here, in particular by prescribing a noise amplitude and/or a statistical noise characteristic. Given random noise, the noise algorithm S determines the concrete functional form of the noise pattern by way of a random number generator, the noise characteristic fixing the statistical probability with which the random number generator generates specific values of the noise pattern. As an alternative to this, the functional form of the noise pattern can be permanently stored in the manner of a fixed pattern noise.

The properties of the noise algorithm S in particular the noise amplitude and the noise characteristic, are based on an equipment-dependent characteristic and quantum physical fundamentals. The "strength" of the noise is determined here as a function of the original acquisition parameters $a_i$ and of the desired image quality measure $M_{mn}$.

A modified raw data record $R'_{mn}$ (m,n=1, 2, 3, . . . ) is produced as a result, its image quality being artificially reduced by comparison with the image quality of the original raw data record $R_m$ to the virtual image quality measure $M_{mn}$. The desired image quality measure $M_{mn}$ is either specified by the user or extracted automatically from a recorded table with prescribed target values.

The simulation module 23 further has a parameter adapting module 27 that is designed to modify the acquisition parameters $a_i$ of the acquisition parameter set $A_m$ assigned to the original raw data record $R_m$ in such a way that the reduced image quality measure $M_{mn}$ is taken into account. In other words, the parameter adapting module 27 produces virtual values for the acquisition parameters $a_i$ which, when applied to the tomography device 3, would produce a raw data record R that would correspond with regard to its image quality to the raw data record $R'_{mn}$ modified by the noise module 26.

For this modification of the acquisition parameters $a_i$, the simulation module 23 reverts to the characteristic database 24, in which the dependence of the image quality on the acquisition parameters $a_i$ and on the patient parameters $p_l$ is stored in the form of characteristics. The acquisition parameters $a_i$ modified by the parameter adapting module 27 form a component of the original parameter set $A'_{mn}$, and are stored together with the patient's data record $P_m$ in the file header of the modified raw data record $R'_{mn}$ as metainformation.

The modified raw data record $R'_{mn}$ is fed to the 3D reconstruction module 25 together with the associated metainformation, that is to say the original parameter set $A'_{mn}$ and the patient data record $P_m$. The final compilation of the original images $B'_{mn}$ is performed here.

The modified raw data record $R'_{mn}$ can be processed like an original raw data record R by a conventional reconstruction system as it is also assigned to the tomography device 3. Thus, a 3D reconstruction algorithm F' that corresponds to the 3D reconstruction algorithm F of the tomography device 3 is also implemented in the 3D reconstruction module 25. This is of great advantage, in particular to the extent that in the case of the reconstruction of the original images $B'_{mn}$ carried out by the 3D reconstruction module 25, the same reconstruction artifacts are produced as occur characteristically and, in particular, together with an insufficient image quality, when original raw data records R are reconstructed. The influence of a change in parameter on the quality of a tomography is thereby simulated particularly realistically.

The modified raw data record $R'_{mn}$ can further be reconstructed using arbitrary values for the acquisition parameters $b_j$. The same modified raw data record $R'_{mn}$ can thus be reconstructed, for example with a different slice thickness, a different increment, etc. In addition, it is also conceivable to reconstruct the same modified raw data record $R'_{mn}$ by using different reconstruction algorithms and/or reconstruction filters.

The original parameter set $A'_{mn}$ assigned to the compiled original image $B'_{mn}$ is supplemented in each case by the 3D reconstruction module 25 by the values used for the acquisition parameters $b_j$.

The original image $B'_{mn}$ fabricated in this way is subsequently stored in the original memory 6 in the way described in conjunction with FIG. 1. The metainformation assigned to the original images $B'_{mn}$, that is to say, in particular, the respective original parameter set $A'_{mn}$ and the assigned patient parameter set $P_m$ and the image quality measure $M_{mn}$, is stored in the file header of the respective image file in accordance with the DICOM standard. The original memory 6 reverts to this information for automatically storing the original images $B'_{mn}$ and for automatic access thereto.

A group $G_m$ of the associated modified raw data record $R'_{mn}$ and the associated original parameter set $A'_{mn}$ is compiled in the way described above in relation to an original raw data record $R_m$ for each original image $B'_{mn}$ to be compiled. The modified raw data records $R'_{mn}$ forming the basis of different original images $B'_{mn}$ of the same group $G_m$ are thereby rendered noisy to a different degree in order to simulate different image quality measures $M_{mn}$.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining an acquisition parameter set, including a number of acquisition parameters, for a medical tomography device, the method comprising:
   making a model image available for selection at a model image compilation apparatus or system;
   using the selection of the model image to select a model parameter set assigned thereto as the acquisition parameter set; and
   compiling, at the model image compilation apparatus or system, a group of a number of model images from a basic tomographic raw data record, each model image corresponding to a different virtual image quality measure, the compiling of each model image including,
      modifying the basic tomography raw data record by way of a noise algorithm for simulating a virtual image quality measure, and
      performing 3D reconstruction on the modified raw data record.

2. The method as claimed in claim 1, wherein a virtual dose value is assigned to the model image as an image quality measure.

3. The method as claimed in claim 2, wherein the model image is preselected from a number of stored model images in accordance with at least one patient parameter.

4. The method as claimed in claim 3, wherein at least one of a weight datum, a body size datum, an age datum, a sex datum, and a body region to be examined is used as a patient parameter.

5. The method as claimed in claim 2, wherein, for the selection, an arbitrary model image of the group is always simultaneously displayed with a standard model image corresponding to a standard image quality.

6. The method as claimed in claim 1, wherein the model image is preselected from a number of stored model images in accordance with at least one patient parameter.

7. The method as claimed in claim 6, wherein at least one of a weight datum, a body size datum, an age datum, a sex datum, and a body region to be examined is used as a patient parameter.

8. The method as claimed in claim 1, wherein all the model images of the same group are always jointly preselected in accordance with each patient parameter and made available for selection.

9. The method as claimed in claim 8, wherein, for the selection, an arbitrary model image of the group is always simultaneously displayed with a standard model image corresponding to a standard image quality.

10. The method as claimed in claim 1, wherein, together with each model image made available for the selection, the image quality measure assigned to this model image is simultaneously displayed.

11. The method of claim 1, further comprising:
   adapting the acquisition parameter set according to the modified raw data record; and wherein
   the compiling step compiles the group of model images from the modified basic tomographic raw data record by performing a 3D reconstruction based on the modified basic tomography raw data record and the adapted acquisition parameter set.

12. The method of claim 1, wherein the modifying step modifies the basic tomography raw data record by adding noise to the basic tomography raw data, the noise being added by way of the noise algorithm.

13. An apparatus for determining an acquisition parameter set, including a number of acquisition parameters, for a medical tomography device having a selection system, comprising:
   a memory in which there is stored a group of a number of model images, each model image corresponding to a different virtual image quality measure, and each model image being compiled by performing 3D reconstruction on a modified raw data record, the modified raw data record being modified by applying a noise algorithm to the basic tomographic raw data record to simulate the different virtual image quality measure; and
   a selection module that is designed to make at least one model image available for selection and, given selection of a model image, to output an original parameter set assigned thereto.

14. The apparatus as claimed in claim 13, further comprising:
   a preselection module that is designed to preselect a model image from the original memory with the aid of at least one patient parameter.

15. The apparatus as claimed in claim 14, including an original compilation system, comprising
   a simulation module, designed to modify the tomographic raw data record by use of the noise algorithm for simulating the virtual image quality measures,
   a downstream 3D reconstruction module, designed to derive a three dimensional model image from the modified tomography raw data record, and
   an original memory for storing the model image.

16. The apparatus as claimed in claim 13, including an original compilation system, comprising:
   a simulation module, designed to modify the tomographic raw data record by use of the noise algorithm for simulating the virtual image quality measures,
   a downstream 3D reconstruction module, designed to derive a three dimensional model image from the modified tomography raw data record, and
   an original memory for storing the model image.

17. The apparatus of claim 13, wherein the applied noise algorithm adds noise to the basic tomography raw data record.

18. A method for determining an acquisition parameter set for a medical tomography device, the acquisition parameter set including a number of acquisition parameters, the method comprising:
   selecting a template image at a template image compilation apparatus or system;
   selecting, at the template image compilation apparatus or system, an original parameter set assigned to the selected template image as the acquisition parameter set;
   modifying, at the template image compilation apparatus or system, a basic tomography raw data record by way of a noise algorithm to simulate a plurality of different virtual image quality measures; and
   compiling, at the template image compilation apparatus or system, a group of a number of template images from the modified basic tomographic raw data record performing 3D reconstruction based on the modffied basic tomography raw data record, each template image corresponding to a different one of the plurality of virtual image quality measures.

19. A method for determining an acquisition parameter set for a medical tomography device, the acquisition parameter set including a number of acquisition parameters, the method comprising:
   selecting, at a template image compilation apparatus or system, a template image;
   selecting, at the template image compilation apparatus or system, an original parameter set assigned to the selected template image as the acquisition parameter set;
   modifying, at the template image compilation apparatus or system, a basic tomography raw data record by adding noise to the basic tomography raw data record to simulate a plurality of virtual image quality measures, the noise being added by way of a noise algorithm; and
   compiling, at the template image compilation apparatus or system, a group of a number of template images from the modified basic tomographic raw data record by performing a 3D reconstruction based on the modffied basic tomography raw data record, each template image corresponding to a different one of the plurality of virtual image quality measures.

* * * * *